United States Patent [19]

Connor et al.

[11] Patent Number: 5,124,347

[45] Date of Patent: Jun. 23, 1992

[54] 3-5-DITERTIARYBUTYLPHENYL-4-HYDROXYMETHYLIDENE DERIVATIVES OF 1,3-DIHYDRO-2H-INDOLE-2-ONES AS ANTIINFLAMMATORY AGENTS

[75] Inventors: David T. Connor; Ila Sircar; Jagadish C. Sircar, all of Ann Arbor, Mich.

[73] Assignee: Warner-Lambert Co., Morris Plains, N.J.

[21] Appl. No.: 738,701

[22] Filed: Jul. 31, 1991

[51] Int. Cl.$^5$ .......................................... C07D 209/34
[52] U.S. Cl. ................................... 514/418; 548/486
[58] Field of Search ................. 548/486, 484; 514/418

[56] References Cited

U.S. PATENT DOCUMENTS

| | | | |
|---|---|---|---|
| 3,161,654 | 12/1964 | Shen . | |
| 3,308,134 | 3/1967 | Plostnieks | 548/486 |
| 3,923,996 | 12/1975 | Hardtmann | 548/486 |
| 4,145,422 | 3/1979 | Winn et al. | 548/486 |
| 4,464,382 | 8/1984 | Tanouchi et al. | 548/183 |
| 4,879,391 | 11/1989 | Howard et al. | 548/486 |

FOREIGN PATENT DOCUMENTS 279263 8/1988 European Pat. Off. .

OTHER PUBLICATIONS

L. R. Mahoney, Agnew. Chem., 81, 555 (1969).
N. M. Emanuel, in: Methods for the Synthesis of and Search for Antitumorigenic Preparations [in Russian], Medgiz, Moscow (1962), p. 22.
D. Harman, Agents' Actions, 1, 3 (1969).
Zungietu et al., Russian Journal of "Chemistry of Heterocyclic Compounds", vol. 9, p. 34 (1973).
L. M. Strigun, et al., *Usp. Khim.* 37 969 (1968).
G. A. Nikiforov et al., *Usp. Khim.* 39, 1369 (1970).

*Primary Examiner*—Donald G. Daus
*Attorney, Agent, or Firm*—Joan Thierstein

[57] ABSTRACT

The present invention is for selected novel compounds which are indoles substituted at the 3-position with [3,5-bis(1,1-dimethylethyl)-4-hydroxyphenyl]methylene as well as pharmaceutical compositions and methods of use thereof. These compounds have activity useful in treating allergies, arthritis, and inflammation.

18 Claims, No Drawings

3-5-DITERTIARYBUTYLPHENYL-4-HYDROXYMETHYLIDENE DERIVATIVES OF 1,3-DIHYDRO-2H-INDOLE-2-ONES AS ANTIINFLAMMATORY AGENTS

BACKGROUND OF THE INVENTION

The present invention is novel compounds which are indoles substituted at the 3-position with [3,5-bis(1,1-dimethylethyl)-4-hydroxyphenyl]methylene and pharmaceutically acceptable acid addition or base salts thereof, pharmaceutical compositions and methods of use thereof. The invneiton compounds are now found to have activity as inhibitors of one or both of cyclooxygenase and 5-lipoxygenase providing treatment of conditions advantageously affected by such inhibition including inflammation, arthritis, pain, fever, and the like. Thus, the present invention is also a pharmaceutical composition or method of use thereof.

Although indoles are known antiinflammatory agents and various compounds having a [3,5-bis(1,1-dimethylethyl)-4-hydroxyphenyl]methylene] substituent are known as antiinflammatory agents, for example, with 3,5-di-tertizry-butyl-4-hydroxyphenyl groups as disclosed in EP Application No. 89 109406.2 and U.S. patent application Ser. No. 499,937 (incorporated herein by reference) now abandoned, the present combination of ring systems, substituents and moieties differs from those previously known. Other compounds having an indole ring system are shown in copending U.S. application Ser. No. 697,823.

Compounds are disclosed having an indole system substituted at the 2- or 3-position in European Publication Number 279,263 and U.S. Pat. No. 4,464,382.

U.S. Pat. No. 3,161,654 discloses an indole ring system substituted through the nitrogen with p-chlorobenzoacyl.

These compound may be distinguished from the compounds of the invention herein by the unique combination of indole and [3,5-bis(1,1-dimethylethyl)-4-hydroxyphenyl]methylene] substituent disclosed here.

[3-[3,5-bis(1,1-dimethylethyl)-4-hydroxyphenyl]-methylene]-1,3-dihydro-2H-indole-2-one is disclosed in the Russian journal of "Chemistry of Heterocyclic Compounds," Vol 9, p. 34 (1973) citing Khim Getrotsikl Soedin, V-9, p 40–44 (Russ), 1973, which further suggests that sterically hundred (shielded) phenols are known to have a number of specific chemical and physiochemical properties having applications as disclosed by L. M. Strigun, et al, Usp; Khim, 37, 969 (1968); G. A. Nikiforov and V. V. Ershov, Usp. Khim, 39, 1369 (1970); L. R. Mahoney, Angew; Chem., 81, 555 (1969); N. M. Emanuel, in: Methods for the Synthesis of and Search for Antitumorigenic Preparations [in Russian], Medgiz, Moscow (1962), p 22; and D. Harman, Agents' Actions, 1, 3 (1969).

SUMMARY OF THE INVENTION

The present invention is a compound of the formula (I)

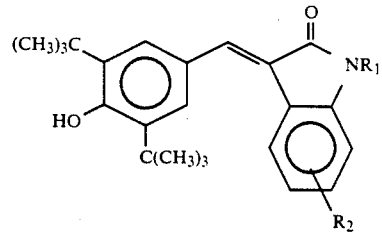

isomers thereof, or a pharmaceutically acceptable salt thereof; wherein
(1) $R_1$ is hydrogen, lower alkyl,

wherein $R_3$ is hydrogen, lower alkyl, phenyl, or substituted phenyl;
(2) $R_2$ is hydrogen, lower alkyl, lower alkoxy, halogen, hydroxy, trifluoromethyl, or $C(O)OR_4$ wherein $R_4$ is hydrogen, lower alkyl, phenyl, or substituted phenyl; with the proviso that $R_1$ an d $R_2$ cannot both be hydrogen and with the further proviso that $R_2$ is not hydrogen when $R_1$ is methyl.

The present invention is also a pharmaceutical compositoin for the treatment of conditions advantageously affected by the inhibition of one or both 5-lipoxygenase and cyclooxygenase with comprises an amount effective for the treatment of the condition of a compound of formula I as define d above or the pharmaceutically acceptable salt thereof together with a pharmaceuticlaly acceptable carrier. Compounds of this invention are inhibitors of the synthesis of the products of one or both of the enzymes 5-liposygenase and cyclooxygenase, and are for the treatment of the conditions meant to include rheumatoid arthritis, osteoarthritis, other inflammatory conditions, psoriasis, pain, allergic diseases, asthma, inflammatory bowel disease, GI ulcers, cardiovascular conditions including ischemic heart disease and alherosclerosis, and ischemia-induced cell damage, particularly brain damage caused by stroke. There conditions can also include acne, sunburn, psoriasis, and eczema. Such conditions are exemplary in nature and are in no way meant to limit the scope of the invention.

Thus, the present invention is also a method for treatment of the condition as noted above in a mammal, including humans, suffering therefrom with a pharmaceutical composition having the compound of formula I

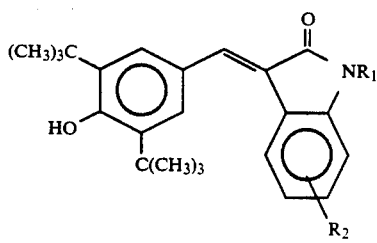

isomers thereof, or a pharmaceutically acceptable salt thereof; wherein
(1) $R_1$ is hydrogen, lower alkyl,

wherein $R_3$ is hydrogen, lower alkyl, phenyl, or substituted phenyl;

(2) $R_2$ is hydrogen, lower alkyl, lower alkoxy, halogen, hydroxy, trifluoromethyl, or $C(O)OR_4$ wherein $R_4$ is hydrogen, lower alkyl, phenyl, substituted phenyl;

in unit dosage form. The invention also provides for use of any such compound of formula I or salt thereof in the manufacture of a medical therapeutic agent.

Pharmaceutical composition of formula I or use of the compound or salt of formula I is meant to include treatment understood to be prophylactic pertinent to the foregoing named conditions.

The most preferred compund of the present invention is a compound of the formula I wherein the compound is 3-[[3,5-bis(1,1-dimethylethyl)-4-hydroxyphenyl]methylene]-1,3-dihydro-7-methoxy-2H-indol-2-one, (2)-.

DETAILED DESCRIPTION OF THE INVENTION

In compounds of formula I, the term "lower alkyl" includes an alkyl group of from one to six carbons such as methyl, ethyl, propyl, butyl, and the like and isomers thereof. The term "substituted phenyl" is a phenyl substituted by from one to three of lower alkyl, lower alkoxy, hydroxy, halogen, trifluoromethyl, $NO_2$, mercapto, lower alkylthio, $NR_{10}R_{11}$ wherein $R_{10}$ and $R_{11}$ are independently hydrogen or lower alkyl.

Appropriate compounds of formula I are useful in free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid and benzenesulfonic acid, p-toluenesulfonic acid, and the like, giving the hydrochloride, sulfate, ethanesulfonate, benzenesulfonate, p-toluenesulfonate, and the like, respectively; or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxylalkylamines such as mono-, di-, or triethyanolamine; amino acids such as arginine and lysine; chlorine; guanidiine; N-methyl glucosamine; n-methyl glucamine; l-glutamine; N-methylpiperazine; morpholine; ethylene diamine; N-benzylphenethylamine; tris(hydroxymethyl)aminoethane; and the like (see for example, "Pharmaceutical Salts", *J. Pharm. Sci.* 66(1):1–19 (1977)). Salts of inorganic bases include sodium, potassium, calcium, or the like.

The acid addition salts of said basic compounds are prepared either by dissolving the free base or acid of compound I in an aqueous or aqueous alcohol solution or other suitable solvent containing the appropriate acid or base, and isolating the salt by evaporating the solution or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention is meant to include each individual isomer and a mixture thereof. The individual isomers may be prepared or isolated by methods known in the art.

The compounds of this invention may also exist in hydrated or solvated form.

Thus, pharmaceutical compositions are prepared from compounds of formula I and salts thereof described as the present invention in unit dosage form comprising the compound either alone or in admixture with a pharmaceutically acceptable carrier appropriately selected from those known.

In determining when a lipoxygenase cyclooxygenase, or dual lipoxygenase/cyclooxygenase inhibitor is indicated, of course, inter alia, the particular condition in question and its severity, as well as the age, sex, weight, and the like of the subject to be treated must be taken into consideration and this determination is within the skill of the attending physician or veterinarian.

A physician or veterinarian of ordinary skill readily determines a subject who is exhibiting allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, cachets, lozenges, pills, powders, or granules. They also may be administered rectally or vaginally in such forms as suppositories or bougies; they may also be introduced parenterally (e.g., subcutaneously, intravenously, or intramuscularaly), using forms known to the pharmaceutical art. They are also introduced directly to an unaffected area (e.g., in the form of eye drops or by inhalation). For the treatment of allergic or inflammatory conditions such as erythema, the compounds of the present invention may also be administered topically in the form of ointments, creams, gels, or the like. In general, the preferred route of administration is orally.

An effective but nontoxic quantity of the compound of formula I or pharmaceutially acceptable salt thereof is employed in treatment. The dosage regimen is selected according to a variety of factors including condition of the subject to be treated, severity of symptoms, and the route of administration. In so proceding, the physician or veterinarian could employ relatively low dosages at first, subsequently increasing the dose until a maximum response is obtained. For convenience, the total daily dosage may be divided and administered in portions during the day if desired.

Initial dosages of the compounds of the invention having formula I or pharmaceutically acceptable salt thereof are orindarily in the range of 20 mg up to 25 g per day, orally, preferably 50 mg to 350 mg per dose orally, given from one to four times daily or as needed. When other forms of administration are employed, equivalent doses are administered.

A suitable dose of a compound of formula I or pharmaceutically acceptable salt thereof for a subject suffering from any condition as described herein before is 0.1 µg to 500 mg of the compound per kilogram body weight. In the case of systemic administration, the dose may be in the range of 0.5 to 500 mg of the compound per kilogram body weight, the most preferred dosage being 0.5 to 500 mg per kilogram body weight administered two to three times daily. In the case of topical administration, e.g., to the skin or eye, a suitable dose may be in the range of 0.1 ng to 100 µg of the compound per kilogram body weight, typically about 0.1 µg/kg.

In the case of oral dosing for the treatment of prophylaxis of arthritis or inflammation in general, due to any cause, a suitable dose of a comound of formula I or II or a pharmaceutically acceptable salt thereof, may be as specified in the preceding paragraph, but most preferably is from 1 to 5 mg of the compound per kilogram of body weight, for example, from 1 to 2 mg per kilogram body weight.

While it is possible for an active ingredient to be administered alone, it is preferable to present it as a pharmaceutical formulation comprising a compound of formula I or a pharmaceutically acceptable acid addition or base salt thereof and a pharmaceutically acceptable carrier therefor. Such formulations constitute a further feature of the present invention.

The formulations, both for verterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the receipient thereof.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtinaed from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate-buffered saline, pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2 \times 10^6$ cells/mL. Cells are incubated and without test agent (in DMSO) (1% DMSO is without effect on arachidonic acid metabolism) for 10 minutes at room temperature. Calcium ionophore A23187 (5 µM) is added and cells are incubated for 7 minutes at 37° C. The reaction is stopped by chilling the tubes on ice for 10 minutes. Cells are separated by centrifugation and the supernatant is stored at −20° C. Aliquots (100 µL) are anlyzed for $LTB_4$ and $PGF_{2\alpha}$ using radioimmunoassay kits as provided by the supplier.

Table 1 contains biochemical data for compounds of formula I obtained from this whole cell assay as amount of inhibition at 10 µM or $IC_{50}s$ which are calculated as the concentration of a test compound in micromoles (µM) causing 50% inhibition of $LTB_4$ or $PGF_{2\alpha}$ formation.

Carrageenan-Induced Rat Foot Paw Edema-2 (CFE-2) Assay: Protocol

Carrageenan solution (1% w/v) is prepared by dissolving 100 mg carrageenan (Marine Colloidal Div., Springfield N.J.) in 10 ml of sterile saline (0.9%) solution (travenol). The solution is vortexed for 30 to 45 minutes. Animals are dosed with compound one hour before carrageenan challenge. Foot paw edema is induced by injecting 0.10 ml of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured five hours after carrageenan. The difference between the five-hour and the initial paw volume is expressed as delta edema. The delta edema for each test group of animals is used to calculate the percent inhibition of edema achieved by the compound at the test dose compared with the vehicle control group. The $ID_{40}$ (the dose at which swelling is inhibited by 40%) is calculated by probit analysis for the dose at which 40 percent inhibition occurs.

Mycobacterium - Induced Rat Footpad Edema Assay (MFE): Protocol

Mycobacterium butyricum (5 mg/ml) is suspended in paraffin oil by sonication for ten minutes in an ice bath. Footpad edema is induced on Day 0 by injecting 0.1 ml of the Mycobacterium mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle one hour before Mycobacterium injection and on Days 1 and 2. Inhibition of swelling is determined by comparing the change in hindpaw volume in compound- and vehicle-treated rats. An $ID_{40}$ (the dose at which swelling is inhibited by 40%) is calculated by probit analysis.

Gastric Ulcerogenicity (UD): Protocol

Male outbred Wistar rats (100–250 mg) are fasted for 24 hours. After fasting, test compounds are administered orally (in 2 mg/kg of 0.5 hydroxypropyl methylcellulose) and the rates are denied access to food and water for six more hours. The rats are then sacrificed with $CO_2$ so that the stomach can be removed, opened along the greater curvature, and evaluated for the presence of gastric ulcers. Resulsts are expressed as the percent of rats with gastric ulcers at a given dose or as the $UD_{50}$ (the dose which causes ulcers in 50% of the rats).

Table 1 also contains biochemical data for compounds of formula I obtained from the CFE and MFE assays.

TABLE 1

| Exam- | IC$_{50}$ (μM) | | CFE | MFE |
|---|---|---|---|---|
| ple | ARBL[a] | ARBC[b] | | |
| 1 | 0.93[c] | 1.5[c] | ID$_{40}$ = 16.0 m/k | 42% @ 10 m/k |
| 2 | 100% @ 10 | N @ 10[d] | | |
| 3 | 100% @ 10 | 32% @ 10 | | |
| 4 | 100% @ 10 | 30% @ 10 | | |
| 5 | 0.43[c] | 6.07[c] | 43% at 10 m/k | 33% @ 10 m/k |
| 6 | 100% @ 10 | N @ 10[d] | | |
| 7 | 100% @ 10 | N @ 10[d] | | |
| 8 | 100% @ 10 | N @ 10[d] | | |
| 9 | 48% @ 10 | N @ 10[d] | | |
| 10 | 100% @ 10 | N @ 10[d] | | |
| 12 | 100% @ 10 | N @ 10[d] | | |

[a] Inhibition of LTB$_4$
[b] Inhibition of PGF$_{2\alpha}$
[c] IC$_{50}$
[d] N = Less than 40% inhibition at 10 μM In addition to the compounds of formula I or a pharmaceutically acceptable salt thereof, the pharmaceutical compositons can also contain other active ingredients, such as cyclooxygenase inhibitors, nonsteroidal antiinflammatory drugs (NSAIDs), peripheral analgesic agents such as zomepirac, diflunisol, and the like. The weight ratio of the compound of the formula I to the second active ingredient may be varied and will depend upon the effective dose of each ingredient. Generally, an effective dose of each will be used. Thus, for example, when a compound of the formula I or II or salt thereof is combined with an NSAID, the weight ratio of the formula I or salt thereof to the NSAID will generally range from about 100:1 to about 1:1000, preferably about 200:1 to 1:200. Combinations of a compound of the formula I or II and other active ingredients will generally also be within the aforementioned range, but in each case, an effective dose of each active ingredient should be used.

Combinations of a compound of the formula I or II or salt thereof and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flubiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivaties having similar analgesic an antiinflammatory properties are also intended to be included in this group.

Thus, "propionic acid derivatives" as defined herein are nonnarcotic analgesics/nonsteroidal antiinflammatory drugs having a free —CH(CH$_3$)COOH or —CH$_2$CH$_2$COOH group (which optionally can be in the form of a pharmaceutically acceptable salt group, e.g., —CH(CH$_3$) COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, ioxepac, furofenac, tropinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g., —CH$_2$COO$^-$Na$^+$) typically attached directly to a ring system, preferably to an aromatic or heteroaromatic ring system.

Thus, "fenamic acid derivatives" as defined herein are nonnarcotic analgesics/nonsteroidal antiinflammatory drugs which contain the basic structure:

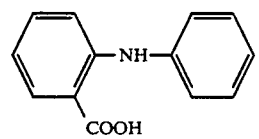

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboyxlic acid derivatives" as defined herein are nonnarcotic analgesics/nonsteroidal antiinflammatory drugs which contain the basic structure:

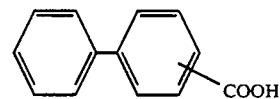

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam, and 4-hydroxy-1,2-benzothiaxne 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesic/nonsteroidal antiinflammatory drugs which have the general formula:

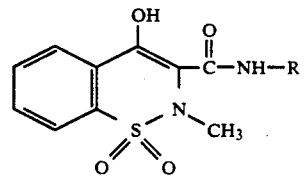

wherein R is an aryl or heteroaryl ring system.

The following NSAIDs may also be used: acemetacin, aminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, closimate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fenetizole mesylate, fenclofenac, fenclorac, fendosal, fenflumizole, fentiazac, feprazone, floctafenine, flunixin, flunoxpropfen, fluproquazone, fopirtoline, fosfosal, furcloprofein, furofenac, flucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate, sodium, meseclazone, microprofen, nabumetone, nictinodole, nimesulide, orpanoxin, oxametacin, oxapadol, oxaprozine, perisoxal citrate, pimeprofen, pimetacin, piproxen, pirazolac, pirfenidone, pirprofen, pranoprofen, proglumetacin maleate, proquazone, pyridoxiprofen, sudixocam, suprofen, talmetacin, talniflumate, tenoxicam, thiazolinobutazine, thielavin B, tiaprofenic acid, tiaramide HCl, tiflamazole, timegadine, tioxaprofen, tolfenamic acid, tolpadol, tryptamid, ufenamate, and zidometacin.

Finally, NSAIDs which may also be used include the salicyclates, specifically aspirin, and the phenylbutazones, and pharmaceutically acceptable salts thereof.

Pharmaceutical compositions comprising the formula I compound or salt thereof may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compound of formula I or salt thereof may also be advantageously combined with an $H_1$ or $H_2$-receptor antagonist, such as for instance, cimetidine, ranitidine, terfenadine, famotidine, temelastine, acrivastine, lorathidine, utrizine tazifylline, azelastine, aminothizdiazoles disclosed in European Patent 81102976.8 and the like compounds such as those disclosed in U.S. Pat. Nos. 4,283,408; 4,362,736; 4,394,508; and European Patent Application 40,696. The pharmaceutical compositions may also contain a $K^+/H^+$-ATPase inhibitor such as omeprazole, disclosed in U.S. Pat. No. 4,255,431, and the like. Each of the references referred to in this paragraph is hereby incorporated by reference.

Generally, the scheme for the preparation of the compounds of formula I above is analogous to that found in the Russian journal of "Chemistry of Heterocyclic Compounds", Vol. 9, pg. 34, 1973. (Khim Geterotsikl Soedin, V-9, p. 40-44 (Russ), 1973 and can be shown as follows:

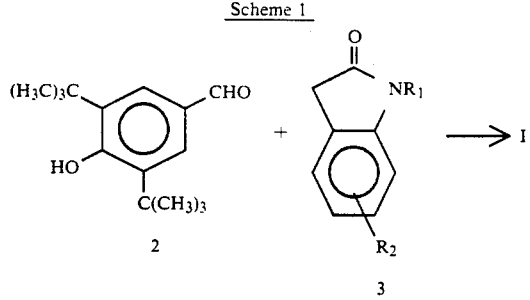

wherein $R_1$ and $R_2$ are as defined above.

That is, a general method of preparation of these compounds is condensation of the aldehyde (2) with a compound having an active methylene group (3). This condensation can be performed in an alcoholic solvent such as ethanol, methanol, or the like in the presence of either a base such as ammonia or piperidine or with a catalytic amount of a mineral acid such as sulfuric acid, HCl, or the like. Alternatively, acetic acid is used as the solvent with either anhydrous sodium acetate or preferably β-alanine. The reactants are heated at reflux for several hours.

If the reaction of Scheme 1 inludes only the formula 3 wherein $R_1$ is hydrogen than subsequent treatment with $R_1$-halide wherein $R_1$ is as defined above other than hydrogen provides a compound of the formula I wherein the $R_1$ is other than hydrogen.

Conditions within the description of Scheme 1 above and variations in the description are known or can be readily determined from analogous reactions known to one of ordinary skill in the art.

Those compounds that contain an acidic proton can be converted to salts via treatment with an organic or inorganic base.

Generally, starting materials are known, commercially available, or can be prepared by known methods.

Under certain circumstances as discussed above, it is necessary to protect either the N or O of intermediates. Introduction and removal of such suitable oxygen and nitrogen protecting groups are well known in the art of organic chemistry; see for example, "Protective Groups in Organic Chemistry," J. F. W. McOmie, *Advances in Organic Chemistry* 3:159-190 (1963); J. F. W. McOmie, *Chem. & Ind.* 603 (1979), and T. W. Greene, "Protective Groups in Organic Synthesis," Wiley (New York) 1981, Chapters 2, 3, and 7.

Examples of suitable oxygen protecting groups are benzyl, t-butyl-protecting groups, ethyoxyethyl, methoxyethoxymethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethyl carbamate, trichloroethoxycarbonyl, vinyloxycarbamate acetyl, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis and t-butyldimethylsilyl being removed by reaction with, for example, tetra-n-butylammonium fluoride.

In the process described herein for the preparation of compounds of this invention, the requirements for protective groups are generally well recognized by one skilled in the art or organic chemistry, and accordingly the use of appropriate protecting groups is necessarily implied by the processes of the schemes herein, although not expressly illustrated.

The products of the reactions described herein are isolated by conventional means such as extraction, distillation, chromatography, and the like.

The invention is further elaborated by the representative examples as follows. Such examples are not meant to be limiting.

EXAMPLE 1

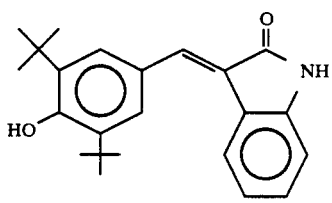

3-[[3,5-bis(1,1-dimethylethyl)-4-hydroxyphenyl]methylene]1,3,-dihydro-2H-indole-2-one, (Z)-*;

A mixture of 3,5-di-tert-butyl-4-hydroxybenzaldehyde (5.28 g; 22.5 mmol), 2-oxindole (3.0 g; 22.5 mmol), and p-toluene sulfonic acid (0.25 g) in toluene (100 ml) is heated under reflux for 18 hours. The reaction mixture is cooled and filtered. The residue is washed with ether and dried @80° C. under vacuum for 18 hours to give 3.4 g (43.2%) of a yellow solid, mp 224°-225° C. (lit. mp 227° C.*).

* This compound was reported in Russian journal of "Chemistry of Heterocyclic Compounds, V-9, p. 34, 1973" (Khim Geterotsikl Soedin, V-9, p. 40–44 (Russ), 1973.

Analysis for $C_{23}H_{27}NO_2$: Calc: C, 79.08; H, 7.73; N, 4.01; Found: C, 78.95; H, 7.72; N, 3.85.

The mother liquor is chromatographed ($SiO_2$, $CHCl_3$/MeOH, 0–1%) to give additional 3.2 g (40.7%) of the desired product.

EXAMPLE 2

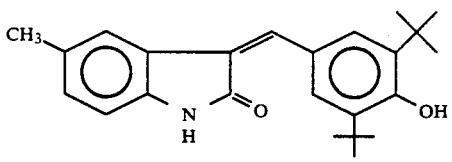

3-[[3,5-Bis(1,1-dimethylethyl)-4-hydroxyphenyl]methylene]-1,3-dihydro-5-methyl-2H-indole-2-one, (Z)

A mixture of 5-methyl-2-oxindole (2.94 g, 0.02 mol), 3,5-di-tertiary-butyl-4-hydroxybenzoldehyde (4.68 g, 0.02 mol), and anyydrous NaOAc (5.75 g, 0.07 mol) in glacial acetic acid (100 mL) was heated to reflux for 18 hours. The cooled reaction mixture was poured into ice-water mixture when a yellow product precipitated out. It was recrystallized from $CH_2Cl_2$—$CH_3OH$-iso-$Pr_2O$ to give the analytical sample. Yield 2.16 g (28.7%), mp 230°-234° C.

Anal. Calcd for $C_{24}H_{29}NO_2$, 0.4 $CH_3OH$: C, 77.88; H, 8.20; N, 3.72. Found: C, 77.96; H, 7.89; N, 3.48.

The filtrate on concentration gave an additional material (1.47 g, 19.5%), mp 232°-234° C. This reaction can also be using beta-alanine instead of NaOAc.

The following compounds were prepared according to the methods described in either Example 1 or in Example 2 using appropriate starting materials and 3,5-di-tert-butyl-4-hydroxybenzaldehyde.

EXAMPLE 3

3-[[3,5-bis(1,1-dimethylethyl)-4-hydroxyphehyl]methylene-2,3-dihydro-2-oxo-1H-indol-1-carboxamide, (Z)-; yield 0.29 g (3.4%); mp 207°-208° C. Starting oxindole was prepared according to U.S. Pat. No. 4,725,616.

EXAMPLE 4

3-[[3,5-bis(1,1-dimethylethyl)-4-hydroxyphenyl[methylene]-1,3-dihydro-1-methyl-2H-indol-2-one, (Z)-; yield 1.20 g (16.5%); mp 145°-148° C. (lit* mp 134° C.; see Example 1 for reference).

EXAMPLE 5

3-[[3,5-bis(1,1-dimethylethyl)-4-hydroxyphenyl]methylene]-1,3-dihydro-7-methoxy-2H-indol-2-one, (Z)-; yield 5.40 g (71%); mp 220°-3° C.

EXAMPLE 6

3-[[3,5-bis(1,1-dimethylethyl)-4-hydroxyphenyl]methylene]-2,3-dihydro-2-oxo-1H-indole-5-carboxylic acid, ethyl ester (Z)-; yield 7.60 g (89%); mp 210°-2° C.

EXAMPLE 7

3-[[3,5-bis(1,1-dimethylethyl-4-hydroxyphenyl]methylene]-1,3-dihydro-7-methyl-2H-indole-2-one, (Z)-; yield 1.57 g (21.6%); mp 238°-41° C.

EXAMPLE 8

3-[[3,5-bis(1,1-dimethylethyl)-4-hydroxyphenyl]methylene]-1,3-dihydro-5-methoxy-1-methyl-2H-indole-2-one, (Z)-; yield 1.45 g (18.4%); mp 167°-8° C.

EXAMPLE 9

3-[[3,5-bis(1,1-dimethylethyl)-4-hydroxyphenyl]methylene]-4-chloro-1,3-dihydro-2H-indole-2-one, (Z)-; yield 0.92 g (18.6%); mp. 239°-242° C.

EXAMPLE 10

3-[[3,5-bis(1,1-dimethylethyl)-4-hydroxyphenyl]methylene]-1,3-dihydro-4-methyl-2H-indole-2-one, (Z)-; yield 0.58 g (8.0%); mp 236°-7° C.

EXAMPLE 11

3-[[3,5-bis(1,1-dimethylethyl)-4-hydroxyphenyl]methylene]-1,3-dihydro-6-methyl-2H-indole-2-one, (Z)-; yield 6.0 g (82.5%); mp 241°-5° C.

EXAMPLE 12

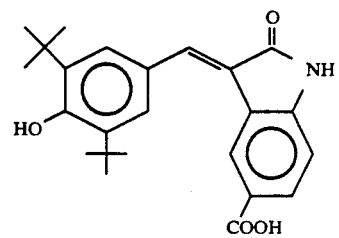

3-[[3,5-bis(1,1-dimethylethyl)-4-hydroxyphehyl]methylene]-2,3-dihydro-2-oxo-1H-indole-5-carboxylic acid, (Z)-, The ester, 3-[[3,5-(1,1-dimethylethyl)-4-hydroxyphenyl]methylene]-2,3-dihydro-2oxo-1H-indole-5-carboxylic acid, ethyl ester (Z)- (Example 6), was hydrolyzed with 1N NaOH solution in methanol for one hour to give the desired compound after several recrystallizations. Yield 0.31 g (13%); mp>285° C.

The starting oxindoles are either commercially available or were synthesized according to the literature procedures.

We claim:

1. A compound of the formula (I)

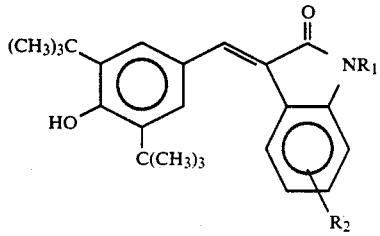

individual isomers thereof, or a pharmaceutically acceptable salt thereof; wherein (1) $R_1$ is hydrogen, lower alkyl,

wherein $R_3$ is hydrogen, lower alkyl, phenyl, or substituted phenyl;

(2) $R_2$ is hydrogen, lower alkyl, lower alkoxy, halogen, hydroxy, trifluoromethyl, or $C(O)OR_4$ wherein $R_4$ is hydrogen, lower alkyl, phenyl, substituted phenyl; with the proviso that $R_1$ and $R_2$ cannot both be hydrogen and with the further proviso that $R_2$ is not hydrogen when $R_1$ is methyl.

2. A compound of claim 1 wherein $R_1$ is hydrogen, methyl, or $CONH_2$ and $R_2$ is hydrogen, lower alkyl, lower alkoxy, or

where in $R_4$ is hydrogen or lower alkyl.

3. A compound of claim 2 which is 3-[[3,5-bis(1,1-dimethylethyl)-4-hydroxyphenyl]methylene]-2,3-dihydro-5-methyl-2H-indole-2-one, (Z)-.

4. A compound of claim 2 which is 3-[[3,5-bis(1,1-dimethylethyl)-4-hydroxyphenyl]methylene]-2,3-dihydro-2-oxo-1H-indol-1-carboxamide, (Z)-.

5. A compound of claim 2 which is 3-[[3,5-bis(1,1-dimethylethyl)-4-hydroxyphenyl]methylene]-1,3-dihydro-7-methoxy-2H-indol-2-one, (Z)-.

6. A compound of claim 2 which is 3-[[3,5-bis(1,1-dimethylethyl)-4-hydroxyphenyl]methylene]-2,3-dihydro-2-oxo-1H-indole-5-carboxylic acid, ethyl ester (Z)-.

7. A compound of claim 2 which is 3-[[3,5-bis(1,1-dimethylethyl)-4-hydroxyphenyl]methylene]-1,3-dihydro-7-methyl-2H-indole-2-one, (Z)-.

8. A compound of claim 2 which is 3-[[3,5-bis(1,1-dimethylethyl)-4-hydroxyphenyl]methylene]-1,3-dihydro-5-methoxy-1-methyl-2H-indole-2-one, (Z)-.

9. A compound of claim 2 which is 3-[[3,5-bis(1,1-dimethylethyl)-4-hydroxyphenyl]methylene]-4-chloro-1,3-dihydro-2H-indole-2-one, (Z)-.

10. A compound of claim 2 which is 3-[[3,5-bis(1,1-dimethylethyl)-4-hydroxphenyl]methylene]-4-methyl-1,3-dihydro-2H-indole-2-one, (Z)-.

11. A compound of claim 2 which is 3-[[3,5-bis(1,1-dimethylethyl)-4-hydroxyphenyl]methylene]-1,3-dihydro-6-methyl-2H-indole-2-one, (Z)-.

12. A compound of claim 2, which is 3-[[3,5-bis-(1,1-dimethylethyl)-4-hydroxyphenyl]methylene]-2,3-dihydro-2-oxo-1H-indole-5-carboxylic acid, (Z)-.

13. A pharmaceutical composition comprising an effective amount of compound of the formula (I)

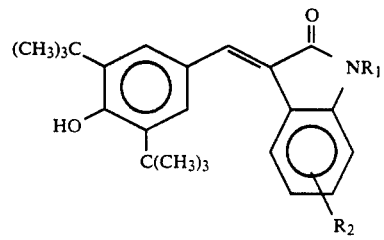

individual isomers thereof, or a pharmaceutically acceptable salt thereof; wherein (1) $R_1$ is hydrogen, lower alkyl,

wherein $R_3$ is hydrogen, lower alkyl, phenyl, or substituted phenyl;

(2) $R_2$ is hydrogen, lower alkyl, lower alkoxy, halogen, hydroxy, trifluoromethyl, or $C(O)OR_4$ wherein $R_4$ is hydrogen, lower alkyl, phenyl, or substituted phenyl.

14. A pharmaceutical composition for treating inflammation comprising an antiiflamatory amount of the compound of claim 13 with a pharmaceutically acceptable carrier.

15. A pharmaceutical composition for treating arthritis comprising an antiarthritic amount of the compound of claim 13 with a pharmaceutically acceptable carrier.

16. A method of treating inflammation in a subject suffering therefrom comprising administration of an antiinflammatory effective amount of a compound of the formula (I)

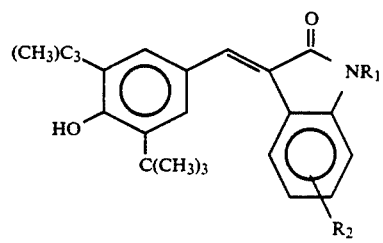

isomer thereof, or a pharmaceutically acceptable salt thereof; wherein (1) $R_1$ is hydrogen, lower alkyl,

wherein $R_3$ is hydrogen, lower alkyl, phenyl, or substituted phenyl;

(2) $R_2$ is hydrogen, lower alkyl, lower alkoxy, halogen, hydroxy, trifluoromethyl, or $C(O)OR_4$ wherein $R_4$ is hydrogen, lower alkyl, phenyl, substituted phenyl; in a unit dosage form.

17. A method of treating arthritis in a subject suffering therefrom comprising administration of an antiinflammatory effective amount of a compound of claim 16 in a unit dosage form.

18. A pharmaceutical composition comprising a compound of the formula I in combination with an NSAID.

* * * * *